(12) United States Patent
Kuang et al.

(10) Patent No.: US 10,808,041 B2
(45) Date of Patent: Oct. 20, 2020

(54) LINCOSAMIDES UNIVERSAL MONOCLONAL ANTIBODY HYBRIDOMA CELL STRAIN AND APPLICATION THEREOF

(71) Applicant: Jiangnan University, Wuxi (CN)

(72) Inventors: Hua Kuang, Wuxi (CN); Lingling Guo, Wuxi (CN); Chuanlai Xu, Wuxi (CN); Liguang Xu, Wuxi (CN); Wei Ma, Wuxi (CN); Liqiang Liu, Wuxi (CN); Shanshan Song, Wuxi (CN); Xiaoling Wu, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/699,048

(22) Filed: Nov. 28, 2019

(65) Prior Publication Data

US 2020/0095337 A1 Mar. 26, 2020

Related U.S. Application Data

(63) Continuation of application No. PCT/CN2018/123952, filed on Dec. 26, 2018.

(30) Foreign Application Priority Data

Dec. 27, 2017 (CN) .......................... 2017 1 14425208

(51) Int. Cl.
*A61K 39/395* (2006.01)
*C07K 16/44* (2006.01)
*G01N 33/94* (2006.01)

(52) U.S. Cl.
CPC .......... *C07K 16/44* (2013.01); *G01N 33/9446* (2013.01); *C07K 2317/92* (2013.01); *G01N 2430/00* (2013.01)

(58) Field of Classification Search
CPC ........................................................ C07K 16/44
See application file for complete search history.

(56) References Cited

FOREIGN PATENT DOCUMENTS

| CN | 101256188 A | 9/2008 |
|----|-------------|--------|
| CN | 101726590 A | 6/2010 |
| CN | 104004718 A | 8/2014 |
| CN | 104897896 A | 9/2015 |
| CN | 108165532 A | 6/2018 |
| WO | 2016044588 A1 | 3/2016 |

*Primary Examiner* — Albert M Navarro
(74) *Attorney, Agent, or Firm* — IPro, PLLC

(57) ABSTRACT

The present disclosure discloses a lincosamides universal monoclonal antibody hybridoma cell strain and application thereof, and belongs to the technical field of food safety immunological detection. According to the present disclosure, a clindamycin chlorine-substituted derivative is used as a hapten, the hapten is coupled with bovine serum albumin (BSA) by an activated ester method to obtain an immunizing antigen, and after being uniformly mixed with a Freund's adjuvant, the immunizing antigen is subcutaneously injected to immunize BALB/c mice; clindamycin is coupled with ovalbumin (OVA) by a carbonyl diimidazole (CDI) method to be used as a coating antigen used for detecting mouse serums and a cell supernatant. The spleen cells of the immunized mice are fused with mouse myeloma cells by a PEG method, and screened by indirect ELISA and indirect competitive ELISA and subcloned three times to obtain a population-selective hybridoma cell strain. The cell strain provided by the present disclosure has relatively good inhibition on clindamycin, lincomycin and pirlimycin, and can meet the demand for lincosamides multi-residue immunoassay products on the market.

10 Claims, 3 Drawing Sheets

LINCOSAMIDES UNIVERSAL MONOCLONAL ANTIBODY HYBRIDOMA CELL STRAIN AND APPLICATION THEREOF

TECHNICAL FIELD

The disclosure herein relates to a lincosamides universal monoclonal antibody hybridoma cell strain and application thereof, and belongs to the technical field of food safety immunological detection

BACKGROUND

Lincosamides drugs have anti-gram-positive aerobic bacteria and gram-positive or negative anaerobic bacteria activities, and lincomycin, clindamycin and pirlimycin are commonly used in veterinary clinic.

Residues of lincosamides drugs in animal-derived foods can cause renal dysfunction and increased drug resistance of gram-positive bacteria. Both China and the European Union have made relevant regulations on the maximum residue limits in animal-derived foods. Therefore, it is urgent to establish a fast, sensitive and accurate method for detecting lincosamides drug residues to ensure the safety of animal foods.

At present, the method for detecting lincosamides drug residues mainly comprises high performance liquid chromatography (HPLC) and liquid chromatography-mass spectrometry (LC/MS), and other instrument detection methods, and immunoassay methods are relatively few. Among them, the instrument detection method is accurate to detect, but the instrument is expensive and complicated to operate, the time is long, and the sample pretreatment is complicated. Compared with the instrument detection method, the immunoassay method has the characteristics of low cost, high throughput, high sensitivity, low requirements for technicians and the like, and is therefore suitable for rapidly screening a large number of samples.

SUMMARY

The present disclosure provides a method for preparing a lincosamides universal monoclonal antibody. Clindamycin, lincomycin and pirlimycin monoclonal antibodies are obtained by preparing a hybridoma cell strain and separating from the hybridoma cell strain. The antibodies have a relatively good detection sensitivity when being used for detecting the clindamycin, lincomycin and pirlimycin, and can be used for establishing an immunological detection method of lincosamides drugs.

A first objective of the present disclosure is to provide a monoclonal cell strain which has been preserved at the China General Microbiological Culture Collection Center on Sep. 5, 2017, the preservation number is CGMCC No. 14691, and the preservation address is No. 3, No. 1 Courtyard, Beichen West Road, Chaoyang District, Beijing.

A second objective of the present disclosure is to provide a method for detecting lincosamides drugs. The method is used to detect the lincosamides drugs through enzyme linked immunosorbent assay using a lincosamides-specific monoclonal antibody secreted by the above monoclonal cell strain CGMCC No. 14691. The lincosamides drugs comprises clindamycin, lincomycin and pirlimycin.

A third objective of the present disclosure is to provide a lincosamides-specific monoclonal antibody, which is secreted by the above monoclonal cell strain CGMCC No. 14691.

The lincosamides-specific monoclonal antibody can be used for analyzing and detecting lincosamides residualin foods.

A fourth objective of the present disclosure is to provide a kit. The kit contains the monoclonal cell strain CGMCC No. 14691 or the lincosamides-specific monoclonal antibody.

The kit is used for analyzing and detecting the residual amount of the lincosamides drugs in foods. The lincosamides drugs comprises clindamycin, lincomycin and pirlimycin.

A fifth objective of the present disclosure is to provide a method for preparing a lincosamides universal monoclonal antibody. The method comprises the steps:

Hapten design: a hapten is prepared by a condensation reaction of β-mercaptopropionic acid with clindamycin. The specific synthetic route is shown in FIG. 1. 9.6 g of active pharmaceutical ingredients of clindamycin is dissolved in 20 mL of dimethyl sulfoxide (DMSO), added with 2.3 g of KOH, and slowly added dropwise with a β-mercaptopropionic acid solution (3.2 g of β-mercaptopropionic acid is dissolved in 10 mL of DMSO) while stirring, an oil bath is heated to 100° C., and the reaction is carried out for 2 h. After the product is naturally cooled to room temperature, 50 mL of water is added, a reaction solution is adjusted to pH 3 with 6 mol/L HCl, and then extracted with 50 mL of dichloromethane, and an extracting solution is dried with anhydrous $Na_2SO_4$, concentrated, and crystallized to obtain a yellow crystal, namely, a target compound, which is identified by mass spectrometry.

Preparation of complete antigen: a clindamycin chlorine-substituted derivative prepared in step (1) is used to be coupled with bovine serum albumin (BSA) by an activated ester method to obtain an immunizing antigen Lin-BSA; the clindamycin is coupled with ovalbumin (OVA) by a carbonyl diimidazole (CDI) method to be used as a coating antigen Lin-OVA.

Animal immunization and titer determination: healthy BALB/c female mice are immunized by adopting a small-dose short-cycle scheme. In the first immunization, 100 μg of a coupling antigen and an equal amount of Freund's complete adjuvant are uniformly mixed and then subcutaneously injected; after 3 weeks, 100 μg of the coupling antigen and an equal amount of Freund's incomplete adjuvant are used to boost the immunization, and then the immunization is boosted once every 3 weeks with a half amount of the coupling antigen; the boosted immunization dose is halved, the product is mixed with an equal volume of normal saline and then the peritoneal immunization is used, and the serum titer is detected and inhibited by indirect competitive ELISA;

Cell fusion and screening: after three days of boosted immunization, the cell fusion is carried out according to the conventional PEG (polyethylene glycol, having a molecular weight of 1450) method. The specific steps are as follows:

The spleens of the mice are aseptically taken and ground and pass through a 200-mesh cell sieve to obtain a spleen cell suspension, and the cell count is performed;

SP2/0 cells are collected and suspended in an RPMI-1640 basal medium for performing the cell count;

Spleen cells and SP2/0 cells are mixed according to a ratio of 10:1 (quantity ratio), centrifuged and then fused with 50% PEG for 1 min, then added with the RPMI-1640 basal medium from slow to fast, centrifuged and then suspended in a RPMI-1640 screening medium containing 20% of fetal calf serum and 2% of 50×HAT, added to a 96-well cell culture plate and placed in a 37° C. incubator containing 5% of $CO_2$ to be cultured. The RPMI-1640 screening medium is half exchanged on the third day of cell fusion, and an RPMI-1640 transition medium containing 20% of fetal calf serum and 1% of 100×HT is fully exchanged on the $6^{th}$ day, and a cell supernatant is taken for screening on the $9^{th}$ day;

the screening is divided into two steps: in the first step, positive cells are screened out by indirect ELISA; in the second step, clindamycin, lincomycin and pirlimycin are selected as standard substances, the inhibition effect of the positive cells is determined by the indirect competitive ELISA, and the positive cells with relatively good inhibition effects on the four standard substances are selected, subcloned by a limiting dilution method, and detected by the same method. The cell strain capable of stably secreting the lincosamides universal monoclonal antibody can be obtained by repeating three times;

Preparation and purification of monoclonal antibody: 8-10 weeks old BALB/c mice are taken, and each mouse is intraperitoneally injected with 1 mL of paraffin oil; after 7 days, each mouse is intraperitoneally injected with 1×10$^6$ hybridoma cells, ascites begins to be collected on the seventh day, the ascites is purified by an octanoic acid-ammonium sulfate method, and the obtained monoclonal antibody is stored at a temperature of −20° C.

The present disclosure has the beneficial effects that: a chlorine substituent of clindamycin designed by the present disclosure is used as the hapten, and coupled with BSA by the activated ester method to obtain an immunogen; the BALB/c mice are immunized, and the active pharmaceutical ingredients of clindamycin are coupled with OVA by the CDI method to obtain the coating antigen used for screening mouse serums and the cell supernatant. Through cell fusion and screening, the cell strain capable of stably secreting the monoclonal antibody, which has relatively good affinity and sensitivity to clindamycin, lincomycin, pirlimycin, is finally obtained. The half inhibition concentrations ($IC_{50}$) of this monoclonal antibody are 0.379 ng/mL for clindamycin, 4.339 ng/mL for lincomycin and 19.314 ng/mL for pirlimycin, respectively. Thus a multi-residue immunoassay method for Lincosamides can be developed.

Biomaterial Preservation

A monoclonal cell strain has been preserved at the China General Microbiological Culture Collection Center on Sep. 5, 2017, the preservation number is CGMCC No. 14691, and the preservation address is No. 3, No. 1 Courtyard, Beichen West Road, Chaoyang District, Beijing.

DETAILED DESCRIPTION

According to the present disclosure, a universal monoclonal antibody with relatively good sensitivity to clindamycin, lincomycin and pirlimycin is finally obtained by immunizing mice by a complete antigen, performing cell fusion, culturing with an HAT selective medium, and screening a cell supernatant by indirect ELISA and indirect competitive ELISA.

Embodiment 1: Preparation of Lincosamides Universal Monoclonal Antibody

Figure 1:
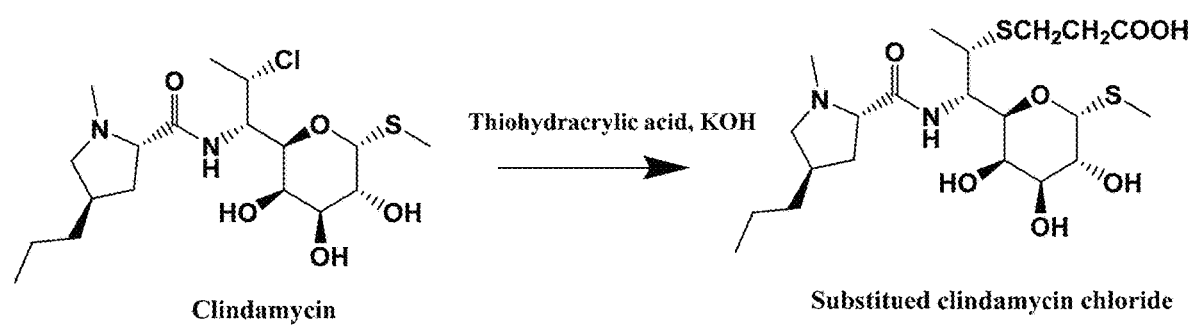
FIG. 1 shows design of a hapten.
Figure 2:
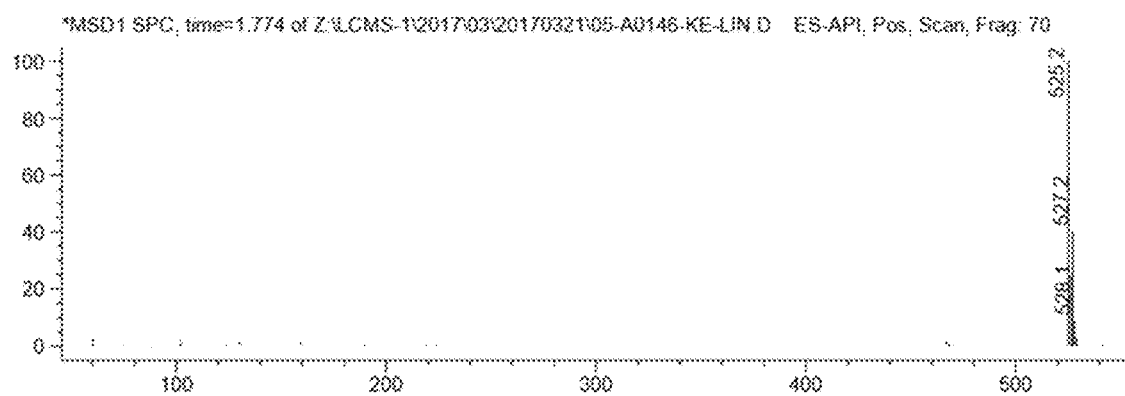
FIG. 2 shows a mass spectrogram of a clindamycin chloride-substituted derivative.
Figure 3:
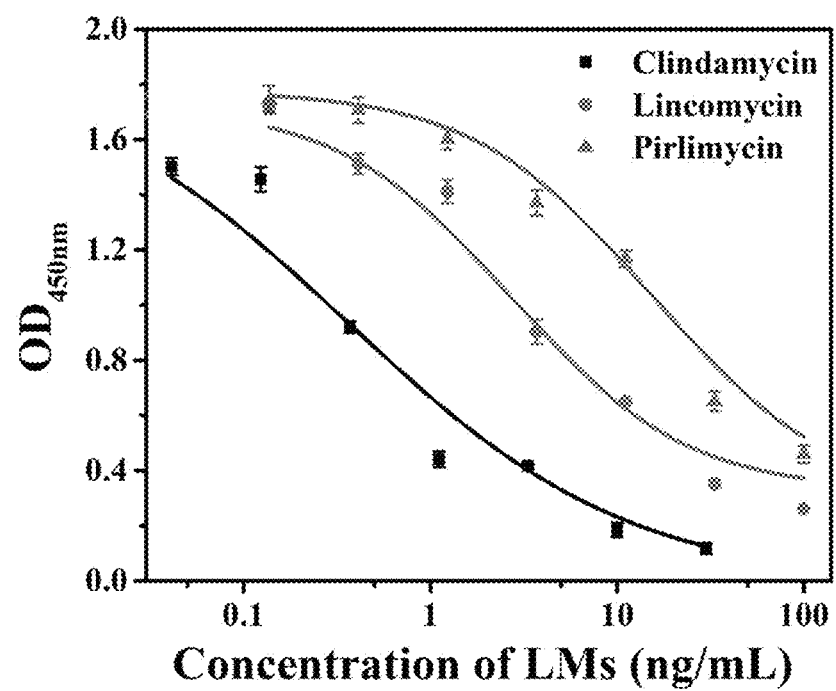
FIG. 3 shows standard curves of an antibody against clindamycin, lincomycin and pirlimycin.

Hapten design a hapten was prepared by a condensation reaction of β-mercaptopropionic acid with clindamycin. The specific synthetic route was shown in FIG. 1. 9.6 g of active pharmaceutical ingredients of clindamycin were dissolved in 20 mL of dimethyl sulfoxide (DMSO), added with 2.3 g of KOH, and slowly added dropwise with a β-mercaptopropionic acid solution (3.2 g of β-mercaptopropionic acid was dissolved in 10 mL of DMSO) while stirring, an oil bath was heated to 100° C., and the reaction was carried out for 2 h. After the product was naturally cooled to room temperature, 50 mL of water was added, a reaction solution was adjusted to pH 3 with 6 mol/L HCl, and then extracted with 50 mL of dichloromethane, and an extracting solution was dried with anhydrous $Na_2SO_4$, concentrated, and crystallized to obtain a yellow crystal, namely, a target compound, which was identified by mass spectrometry.

Preparation of complete antigen: a clindamycin chlorine-substituted derivative was used to be coupled with bovine serum albumin (BSA) by an activated ester method to obtain an immunizing antigen Lin-BSA; the clindamycin was coupled with ovalbumin (OVA) by a carbonyl diimidazole (CDI) method to be used as a coating antigen Lin-OVA. The specific synthesis method was as follows:

Synthesis of Lin-BSA: 10 mg of the hapten was weighed and dissolved in 3 ml of a 0.1 M pH 6.0 2-(N-morpholine) ethanesulfonic acid (MES) monohydrate solution; 24 mg of N-hydroxysuccinimide was firstly added under constant stirring, and after 15 min, 31 mg of 1-ethyl-3-(3-dimethyl-aminopropyl-carbodiimide) was added; an activating solution was obtained by stirring for 2 h at room temperature; 20 mg of BSA was weighed, and dissolved in 1 ml of a 0.1 M pH 9.0 carbonate buffer solution; the activating solution was added dropwise under constant stirring to react at room temperature for 4 h, and then a reaction solution was dialyzed with a 0.01 M pH 7.4 phosphate buffer solution to obtain Lin-BSA.

Synthesis of Lin-OVA: 10 mg of active pharmaceutical ingredients of clindamycin and 29.89 mg of CDI were respectively weighed and completely dissolved in 2 ml of anhydrous N,N-dimethylformamide (DMF), and activated at room temperature for 5 h; the activating solution was added dropwise to an OVA solution (20 mg/ml, 0.1 M pH 9.0 carbonate buffer solution) to react at room temperature overnight, and a reaction solution was dialyzed with a 0.01 M pH 7.4 phosphate buffer solution to obtain Lin-OVA.

Animal immunization and titer determination: healthy BALB/c female mice were immunized by adopting a small-dose short-cycle scheme. In the first immunization, 100 μg of a coupling antigen and an equal amount of Freund's complete adjuvant were uniformly mixed and then subcutaneously injected; after 3 weeks, 100 μg of the coupling antigen and an equal amount of Freund's incomplete adjuvant were used to boost the immunization, and then the immunization was boosted once every 3 weeks with a half amount of the coupling antigen; the boosted immunization dose was halved, the product was mixed with an equal volume of normal saline and then the peritoneal immunization was used, and the serum titer was detected and inhibited by indirect competitive ELISA;

The specific ELISA procedure was as follows:
Coating: the coating antigen was subjected to gradient dilution with a 0.05 M pH 9.6 carbonate buffer solution, and incubated at 37° C. for 2 h at 100 μL/well.

Washing: a solution in a plate was decanted, and 200 μL of a PBST solution was injected into each well, placed on a shaker to shake for 3 min, spin-dried, and washed 3 times. The following washing method was the same.

Blocking: After patting dry, 200 μL of a blocking buffer was added to each well, and incubated at a temperature of 37° C. for 2 h. After washing, the product was dried to be ready for use.

Loading: PBS was added to the upper half part of an ELISA plate at 50 μL/well (the upper half part is called a zero standard substance), different concentrations of lincosamides standard substances were added to the lower half part, antiserums were subjected to gradient dilution from 1:1000 at 50 μL/well (the lower half part becomes an added standard substance), and the upper and lower parts were correspondingly added to the wells of different dilution gradients of coating antigens, and incubated at a temperature of 37° C. for 30 min; after fully washing, a mouse secondary antibody diluted according to 1:3000 was added at 100 μL/well, incubated at a temperature of 37° C. for 30 min, washed and then patted dry.

Color development: the ELISA plate was taken out, and fully washed, and then 100 μL of a color developing solution (the ratio of TMB to a substrate liquid is 1:5) was added to each well to react at a temperature of 37° C. for 15 min in the dark.

Stopping and determination: the ELISA plate was taken out, 50 μL of a stop solution (2 mol/L sulfuric acid) was added to each well to stop the reaction, and then the absorbance A450 of each well was determined by an ELISA reader.

Result interpretation: the highest dilution factor of the corresponding serum having an OD value 2.1 times or more (i.e., P/N≥2.1) of the OD value of a negative serum control well is the ELISA titer of the serum. By comparing the upper and lower parts, the concentration where the OD value of the added standard substance is half that of the zero standard substance is the concentration of the added standard substance.

Cell fusion and screening: after three days of boosted immunization, the cell fusion was carried out according to the conventional PEG (polyethylene glycol, having a molecular weight of 1450) method. The specific steps were as follows:

The spleens of the mice were aseptically taken and ground and passed through a 200-mesh cell sieve to obtain a spleen cell suspension, and the cell count was performed;

SP2/0 cells were collected and suspended in an RPMI-1640 basal medium for performing the cell count;

Spleen cells and SP2/0 cells were mixed according to a ratio of 10:1 (quantity ratio), centrifuged and then fused with 50% PEG for 1 min, then added with the RPMI-1640 basal medium from slow to fast, centrifuged and then suspended in a RPMI-1640 screening medium containing 20% of fetal calf serum and 2% of 50×HAT, added to a 96-well cell culture plate and placed in a 37° C. incubator containing 5% of $CO_2$ to be cultured. The RPMI-1640 screening medium was half exchanged on the third day of cell fusion, and an RPMI-1640 transition medium containing 20% of fetal calf serum and 1% of 100×HT was fully exchanged on the $6^{th}$ day, and a cell supernatant was taken for screening on the $9^{th}$ day;

the screening was divided into two steps: in the first step, positive cells were screened out by indirect ELISA; in the second step, clindamycin, lincomycin and pirlimycin were selected as standard substances, the inhibition effect of the positive cells was determined by the indirect competitive ELISA. The positive cells with relatively good inhibition effects on the four standard substances were selected, subcloned by a limiting dilution method, and detected by the same method. The cell strain capable of stably secreting the lincosamides universal monoclonal antibody can be obtained by repeating three times;

Preparation and identification of monoclonal antibody: 8-10 weeks old BALB/c mice were taken, and each mouse was intraperitoneally injected with 1 mL of paraffin oil; after 7 days, each mouse was intraperitoneally injected with $1 \times 10^6$ hybridoma cells, ascites begun to be collected on the seventh day, the ascites was purified by an octanoic acid-ammonium sulfate method, and the obtained monoclonal antibody was stored at a temperature of −20° C.

Using the indirect competitive ELISA and indirect ELISA, the $IC_{50}$ of the monoclonal antibody on clindamycin, lincomycin and pirlimycin is 0.379 ng/mL, 4.339 ng/mL and 19.314 ng/mL, respectively by determination; and the demand for lincosamides immunoassay products on the market can be met.

What is claimed is:

1. A monoclonal cell strain, preserved at the China General Microbiological Culture Collection Center on Sep. 5, 2017, wherein the preservation number is CGMCC No. 14691, and the preservation address is No. 3, No. 1 Courtyard, Beichen West Road, Chaoyang District, Beijing, China.

2. A lincosamides-specific monoclonal antibody, wherein the lincosamide-specific monoclonal antibody is produced by secretion of the monoclonal cell strain according to claim 1.

3. A method for using the lincosamides-specific monoclonal antibody according to claim 2, comprising analyzing and detecting lincosamides residues using the lincosamides-specific monoclonal in food safety detection.

4. The method according to claim 3, further comprising detecting a lincosamides drug by enzyme-linked immunosorbent assay using the lincosamides-specific monoclonal antibody.

5. The method according to claim 4 wherein the lincosamides drug comprises clindamycin, lincomycin or pirlimycin.

6. The method according to claim 4, wherein the lincosamides drug comprises clindamycin, lincomycin and pirlimycin.

7. The method according to claim 3, wherein the lincosamides-specific monoclonal antibody is applied to a detection kit.

8. The method according to claim 7, comprising using the kit for detecting the lincosamides drug.

9. The method according to claim 8, wherein the lincosamide drug comprises clindamycin, lincomycin or pirlimycin.

10. A kit comprising the lincosamides-specific monoclonal antibody according to claim 2.

* * * * *